United States Patent [19]
Nashner et al.

[11] Patent Number: 4,830,024
[45] Date of Patent: May 16, 1989

[54] APPARATUS AND METHOD FOR DETERMINING THE PRESENCE OF VESTIBULAR PERILYMPH FISTULAE AND OTHER ABNORMAL COUPLING BETWEEN THE AIR-FILLED MIDDLE EAR AND THE FLUID-FILLED INNER EAR

[76] Inventors: Lewis M. Nashner, 366 N.E. Merges Dr.; F. Owen Black, 02425 S.W. Military Rd.; David J. Lilly, 685 N.W. Melinda, all of Portland, Oreg. 97212

[21] Appl. No.: 220,411

[22] Filed: Jul. 19, 1988

Related U.S. Application Data

[63] Continuation of Ser. No. 895,783, Aug. 12, 1986, abandoned, which is a continuation-in-part of Ser. No. 873,125, Jun. 11, 1986, Pat. No. 4,738,269, which is a continuation of Ser. No. 408,184, Aug. 16, 1982, abandoned.

[51] Int. Cl.$^4$ .............................................. A61B 5/10
[52] U.S. Cl. .................................... 128/787; 128/746
[58] Field of Search ................ 128/746, 747, 774, 782

[56] References Cited
PUBLICATIONS

Nosher, Sensory Feedback in Human Posture Control, MUT-70-3, Thesis, MIT, Jun. 1970.

*Primary Examiner*—Kyle L. Howell
*Assistant Examiner*—John C. Hanley
*Attorney, Agent, or Firm*—Bromberg & Sunstein

[57] ABSTRACT

A method for determining the presence of perilymph fistula or other abnormal coupling between a subject's middle ear and inner ear. The subject is placed on a support surface that is sway-stabilized about an axis that is co-linear with the subject's ankle joints. After the subject has assumed a position in equilibrium, a controlled changed in air pressure is introduced to the external canal of one of the subject's ears. It is then determined whether the controlled change in pressure produces a significant subject sway response. In an alternative embodiment, the sway response is monitored with the subject placed on a support surface that is sway-stabilized about an axis that is perpendicular to the axis that is co-linear with the subject's ankle joints.

6 Claims, 4 Drawing Sheets

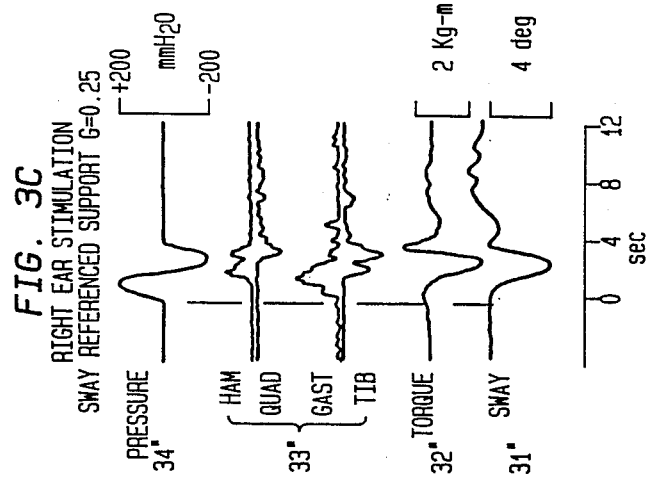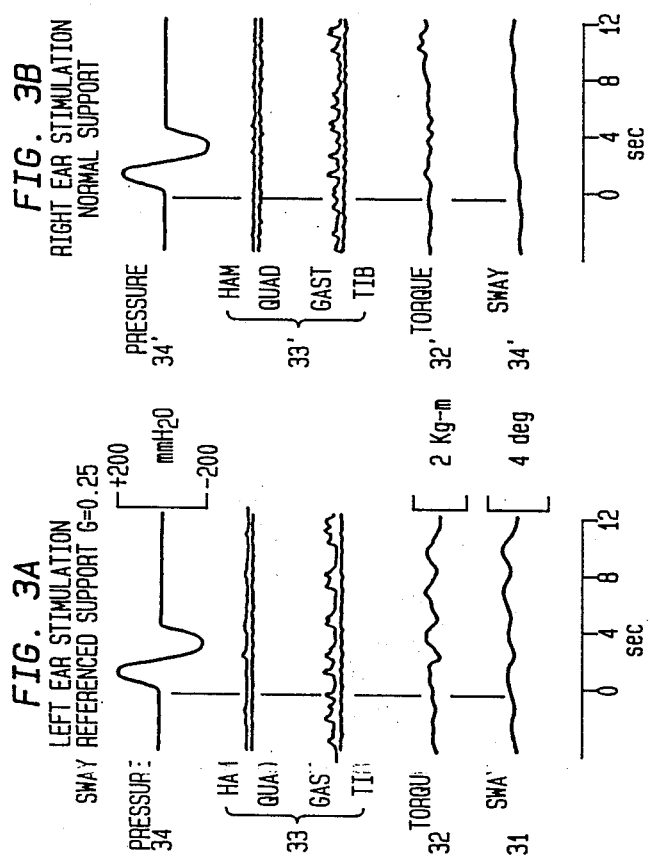

APPARATUS AND METHOD FOR DETERMINING THE PRESENCE OF VESTIBULAR PERILYMPH FISTULAE AND OTHER ABNORMAL COUPLING BETWEEN THE AIR-FILLED MIDDLE EAR AND THE FLUID-FILLED INNER EAR

This is a continuation of co-pending application Ser. No. 895,783 filed on Aug. 12, 1986 now abandoned, which is a continuation-in-part of Ser. No. 873,125, filed June 11, 1986, now U.S. Pat. No. 4,738,269, which is a continuation of Ser. No. 408,184 (now abandoned), filed Aug. 16, 1982, for an invention of Lewis M. Nashner, one of the inventors herein.

TECHNICAL FIELD

This invention relates generally to methods and devices for providing non-invasive, sensitive, and reliable tests for the presence of perilymph fistulae and other abnormal coupling between the middle ear and the inner ear. Such methods and devices are to be used as diagnostic tools for patients with symptoms of dysequilibrium, vertigo, and/or motion sickness.

BACKGROUND ART

A perilymph fistula is an abnormal connection, i.e., a small hole in the round or oval window, between the perilymph fluid of the inner ear and the middle ear air space. The first described cases of perilymph fistulas were a consequence of otic capsule bone erosion associated with middle ear and mastoid infections (Schuknecht, 1974). Fee (1968) was the first to report oval and round window fistulas caused by head trauma. Patients with both types of perilymph fistulas report episodes of dizziness, vertigo, dysequilibrium, tinitus, and hearing loss. Other abnormal couplings between the air-filled middle ear and the fluid-filled inner ear involve softening of the otic capsule, evulsion of the stapes footplate, deformation of the ossicular chain, and fractures of the ossicles or temporal bone. In some cases these problems are congenital rather than adventitious.

A reliable and non-invasive clinical test for perilymph fistulas and other abnormal communication between the middle and inner ear is not possible with the devices and methods currently available to clinicians. Because the history and symptoms reported by the patient with a middle ear perilymph fistula often resemble those reported by patients with other forms of inner ear vestibular disorders, symptoms and history do not provide a reliable means to determine whether or not the patient has a perilymph fistula. According to a number of clinicians specializing in vestibular disorders, a definitive diagnosis of a post-traumatic middle ear perilymph fistula can be made only by direct inspection of the middle ear through surgical intervention, i.e., tympanotomy (Goodhill, 1980; Healy, 1974 & 1976; Simmons, 1982; Lehrer, 1984; Kohut, 1979; Nomura, 1984; Singleton, 1978). Hence, a reliable non-invasive perilymph fistula test would eliminate the need for exploratory surgery in many cases.

Several groups of individuals have attempted to develop non-invasive and yet reliable tests for the presence of middle ear perilymph fistulas. Daspit, et al., (1980) used an impedance bridge to introduce controlled changes in external ear canal pressure while recording the patient's eye movement responses using electronystagmography. These clinicians used air pressure stimuli ranging from $-600$ $+300$ millimeters of water. Supance (1983) and Healey, et al. (1979) used similar techniques. In all of these instances, however, the reliability of the test was found to be relatively low, ranging from a high of 75% to a low of 37%. Noting the high incidence of postural instability among fistula patients, Lehrer, et al. (1984) used the so called Quix test in which body sway responses to external ear canal pressure stimuli are measured with the subject standing freely. In the Quix test, however, the subject stands on a fixed surface and within a normally fixed visual surround. Hence, this method does not test the subject's postural response to external ear canal pressure at a time when the posture control system is maximally sensitive to vestibular inputs.

A number of signal processing methods exist for determining whether or not a stimulus produces statistically significant changes in a measured variable. One such technique is termed "pulse triggered averaging". The stimulus in this technique consists of a train of discrete mono or biphasic pulses. The measured variable is divided into segments that are time locked to the onset of the stimulus pulses. The segments are then averaged. A significant change in the properties of the measured variable correlated with the onset of pulses indicates that the measured variable is influenced by the stimulus. A second technique uses continuously varying sinusoidal or step-like stimuli and "linear systems analysis" to determine whether or not temporal properties of the measured variable are significantly correlated with the stimulus (for example; Brown, et al., 1982).

DISCLOSURE OF INVENTION

The present invention provides a method and apparatus for determining the presence of perilymph fistulas and other forms of abnormal coupling between the middle ear and the inner ear. Controlled air pressure stimuli are introduced to the external auditory canal of an erect standing subject while the subject's posture control system is maximally sensitive to inputs from the inner ear vestibular system. Maximum sensitivity to vestibular inputs is achieved by eliminating vision and then gradually disrupting somatosensory orientation inputs provided by contact between the feet and the support surface.

In accordance with methods of the present invention, the subject assumes an erect standing position in equilibrium on a support surface. The support surface is rotatable about a horizontal axis approximately 2 inches above the surface. The subject's feet are placed such that the support surface and ankle joint rotation axes are approximately co-linear. To eliminate visual orientation inputs, the subject's eyes are closed. To eliminate accurate orientation inputs derived from the somatosensory senses in contact with the support surface, angular sway displacements of the subject's body from the assumed erect equilibrium position in the antero-posterior plane are measured and the support surface rotated in direct proportion to this measured quantity. In the previous Nashner application of which this application constitutes a continuation-in-part, this was called the "stabilized" support surface condition. Subsequent to this application, however, we have altered terminology and now refer to this as the "sway-referenced" support surface condition, because the orientation of the surface is referenced to the sway angle of the subject's center of gravity rather than fixed in relation to the gravity vertical.

Some patients suspected of having perilymph fistulas are unable to maintain their balance under sway-referenced support surface conditions. Therefore, it is sometimes necessary to modify the extent to which somatosensory and visual orientation inputs are removed. Patient's requiring vision to maintain their balance are tested eyes open. To provide the individual patient with sufficient somatosensory orientation information to maintain standing equilibrium, the support surface is rotated in fractional relation to the measured sway orientation of the subject's center of body gravity. For example, when the subject's body sways forward 4 degrees, the support surface is rotated forward one-half as much or 2 degrees. We refer to this fractional relation between body sway and support surface rotation as the sway-reference "gain".

Pressure within the middle ear space can be changed by introducing controlled changes in air pressure to the external canal of the ear. There are potentially at least two pathways to the vestibular system. The relative contribution of each of these pathways is, to a certain extent, dependent upon the integrity of the tympanic membrane and the middle-ear transmission system.

Specifically, with a perforation of the tympanic membrane or with an intact tympanic membrane and complete interruption of the ossicular chain, the only mechanism for stimulating vestibular transducers is through changes in the middle ear pressure. In contrast, an intact tympanic membrane and a compliant middle-ear transmission system also permits us to move perilymphatic fluid through direct piston action of the stapes footplate.

The interaction of these two coupling modes currently is not clear for subjects with normal hearing and for patients with various types of middle-ear and tympanic-membrane problems. If the subject has one or more abnormal connections between the inner ear perilymph fluid and the middle ear space (perilymph fistula), then the vestibular sense organs will be stimulated by the pressure change. With the subject's posture control system maximally sensitive to vestibular inputs, the presence of a perilymph fistula is highly probable if the subject has a postural reaction to the external ear canal pressure stimulus.

The accuracy and reliability of this perilymph fistula test is significantly greater than that possible with currently available clinical methods. Furthermore, by altering what we call the sway-reference "gain" of the support surface motions, a threshold level for perilymph fistula sensitivity can be established.

In a preferred embodiment of the present invention, the subject stands on a support surface, which rests on three or more vertical force transducers. A digital computer samples signals from the force transducers and calculates the front-back and side to side positions of the center of force exerted by the subject's feet against the surface and the front-back angular position of the subject's body center of gravity in relation to the ankle joints. An electric servomotor positions the support surface about a rotational axis parallel and approximately 2 inches above the surface. The computer controls on a continuous basis the rotational position of the support surface, such that the surface rotates in relation to the calculated position of the center of vertical pressure, the angular orientation of the subject's center of body gravity, or a combination of the two variables. Air pressure changes to the external auditory canal of an ear are introduced through a tube. The tube is connected to a air pressure generating source which is also controlled on a continuous basis by the computer.

In a preferred protocol based on the above preferred embodiment, the computer calculates the anteroposterior and lateral positions of the center of vertical force and the anteroposterior angular position of the subject's body center of gravity in relation to the ankle joints. The support surface is fixed in the horizontal position by setting the sway-reference gain to 0.0. The statistical properties of anteroposterior and lateral movements of the center of vertical force are calculated. Then, a series of brief controlled changes in ear canal pressure are introduced and the statistical properties of anteroposterior and lateral movements of the center of vertical force re-calculated by the computer. Significant increases in motions of either one or both of the anteroposterior and lateral center of vertical force positions following imposition of the pressure stimuli, as determined by standard statistical tests, indicates a high probability of perilymph fistula, and the protocol is terminated.

If the imposition of pressure stimulation with the support surface fixed in the horizontal position does not produce a significant postural response, the above proceedure is repeated with the sway-reference gain increased to 0.12. If a statistically significant postural response is again not demonstrated, the above proceedure is repeated with the sway-reference gain increased in subsequent trials to 0.25, 0.50, 0.75, and then 1.0. Statistically significant increases in motions of either one or both center of vertical force positions correlated with the pressure stimuli at one of these sway-reference gains indicates a high probability of perilymph fistula. The absence of pressure correlated increases in postural activity at any of the sway-refernce gains indicates that a perilymph fistula in the stimulated ear is highly unlikely.

In an alternative embodiment of the invention, information about the patient's postural activity is enhanced by also measuring electromyographic (EMG) activity of a plurality of leg and lower trunk muscles supporting the body against gravity.

BRIEF DESCRIPTION OF THE DRAWINGS

FIG. 3 illustrates the sequence of events measured during a typical perilymph fistula test conducted according to a possible embodiment of the present invention.

DESCRIPTION OF SPECIFIC EMBODIMENTS

In co-pending application Ser. No. 873,125, filed 6-11-86, a continuation of Ser. No. 408,184, filed Aug. 16, 1982, for an invention of Lewis M. Nashner, one of the inventors herein, a method and apparatus were described which force a subject to use vestibular orientation information while maintaining a position in equilibrium. Somatosensory (inputs from contact with the support surface) and visual orientation inputs to the subject are masked by: (1) placing the subject on a movable support surface, (2) having the subject stand eyes closed, (3) measuring the spontaneously occurring displacements of the subject away from the equilibrium position, and then (4) moving the support surface in functional relation to the displacement of the subject from equilibrium.

In a preferred embodiment of the Nashner invention, the subject stands erect with his ankle joints co-linear with the rotational axes of support surface. According to a preferred protocol of the Nashner invention, the support surface rotates in direct proportion to the rotational displacements of the subject's center of body gravity in relation to the feet. This is called the "sway-referenced" support surface condition, because the orientation of the surface is referenced to the sway orientation of the subject rather than to gravity. This technique makes the orientation information derived from somatosensory inputs (inputs from contact with the support surface) inaccurate and therefore unreliable for controlling equilibrium. Under sway-referenced support surface conditions with eyes closed, a subject standing on the platform support surface is forced to rely on vestibular inputs to maintain his position in equilibrium. Under these conditions, therefore, the patient is maximally sensitive to vestibular stimuli.

Utilizing the present invention, a relatively straightforward test protocol can determine whether or not a subject has a perilymph fistula in one or both ears or other abnormal coupling between the middle-ear and the inner-ear.

Figure 1:
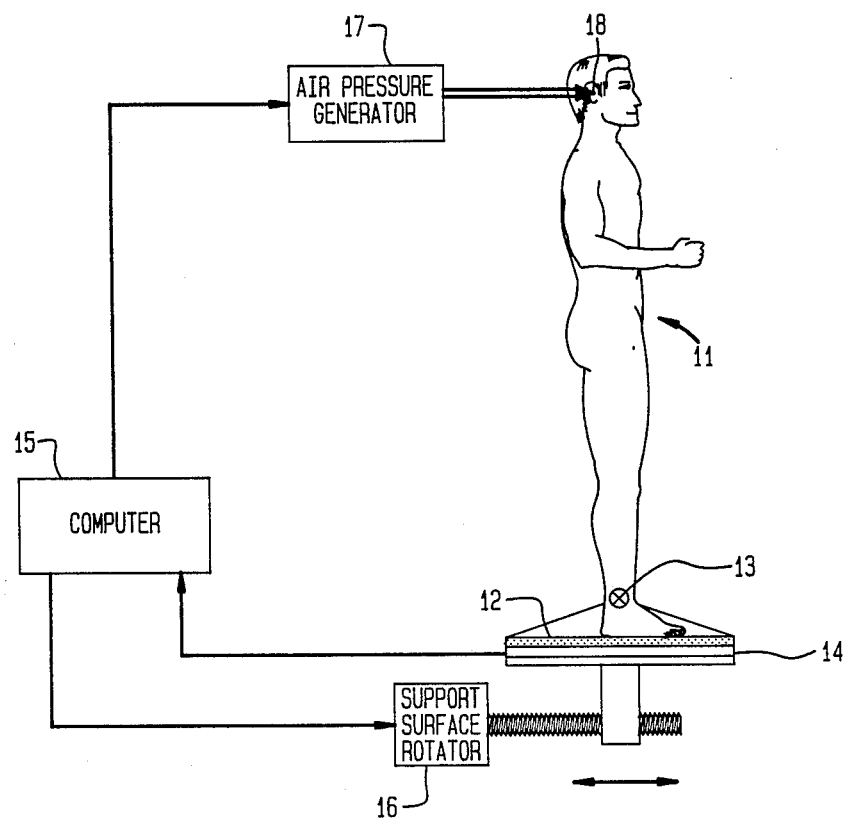
FIG. 1 shows a schematic block diagram of the principal components of a possible embodiment of an apparatus according to the present invention.
Figure 2:
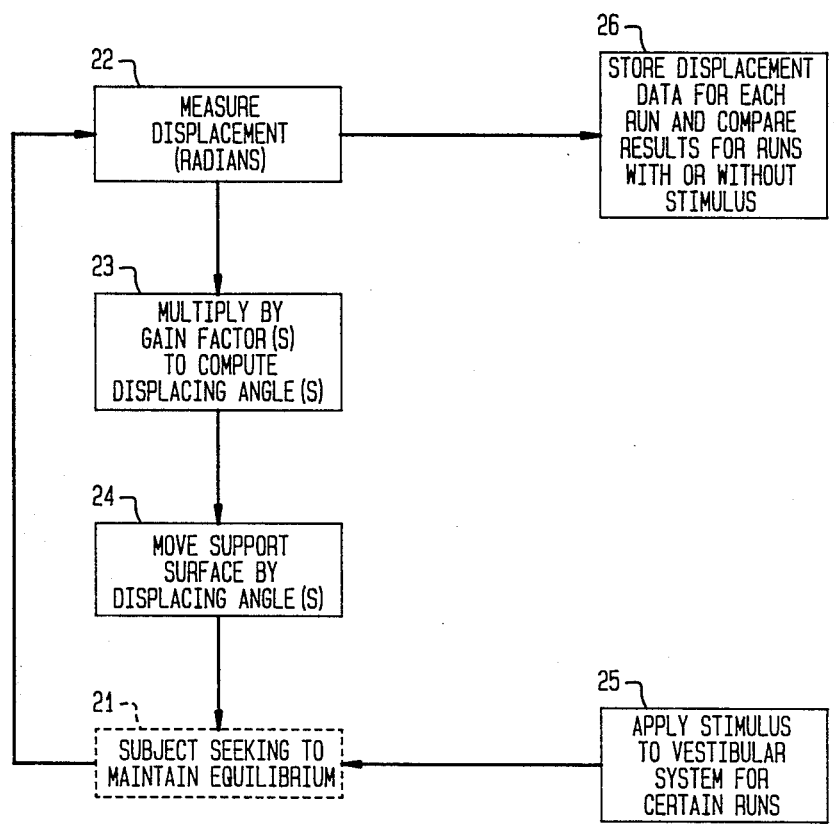
FIG. 2 shows a block diagram of the principal steps of a possible embodiment of a method according to the present invention.

FIG. 1 shows a schematic block diagram of the principal components of a possible embodiment of an apparatus according to the present invention. In this embodiment, the subject 11 stands erect in a position of equilibrium on a support surface 12, which is rotatable about an axis 13 co-linear with the ankle joints. The support surface rests on vertical force transducers 14, the signals from which are transmitted to the computer 15 for calculating anteroposterior and lateral positions of the center of vertical force and angular displacements of the subject's center of body gravity from the equilibrium position. The computer generates signals which rotate the support surface 16 in proportion to the computed angular displacement of the subject's center of body gravity. Finally, the computer activates a device which generates controlled changes in air pressure 17 to one of the subject's ears 18, and then computes whether or not pressure changes produce correlated and significant increases in one or more of the measured variables of postural activity.

Figure 4:
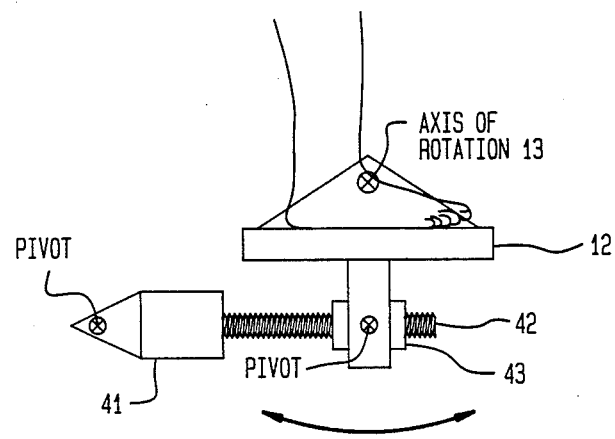
FIG. 4 illustrates a possible embodiment of means for controlling the rotational position of the support surface.

FIG. 4 shows one means for controlling the rotational position of the support surface 12, using a system comprising an electric motor 41, lead screw 42, and a ball nut 43. Rotations of the motor and lead screw move the ball nut back and forth and thus rotate the support surface.

Figure 5:
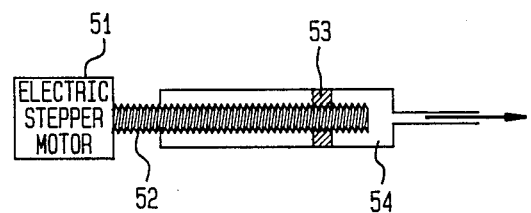
FIG. 5 illustrates a possible embodiment of means for controlling the air pressure within the pneumatic tube.

FIG. 5 shows one means for generating controlled changes in air pressure within the external ear canal using a pneumatic tube. A system comprising an electric stepper motor 51, lead screw 52, and ball nut 53, moves a piston within a pneumatic cylinder 54. The movements of the piston changes the volume of the tube, thus compressing the air and changing the pressure. The means for measuring air pressure within a volume and for accurately maintaining a given level of pressure using pressure feedback control are well-known in the art.

In a preferred embodiment of the perilymph fistula test, the standing subject is positioned on the rotatable support surface 12 with eyes closed and ankle joint axis co-linear with the support surface rotation axis 13 as shown in FIG. 1.

The pneumatic tube is placed the one of the subject's ears 18. The angular orientation of the subject's center of body gravity in relation to the ankles in the anteroposterior plane of motion is calculated from the forceplate 14 measurements. The angular measure is multiplied by the sway-refernce gain factor. Then, the support surface 12 is rotated in direct proportion to the calculated angular measure.

FIG. 3 illustrates the sequence of events measured during a perilymph fistula test conducted according to a possible embodiment of the present invention. Three measures of the subject's displacements from equlibrium are recorded by the computer for an interval of time sufficient to establish baseline levels of postural activity. After the three activity baselines are established, one or a series of brief pressure changes are introduced to the ear, while recording of the three measures of postural activity continues. Finally, mean levels of activitiy in each of the three measures of stability are computed during a 500 millisecond interval following each pressure stimulus.

In part A of FIG. 3, the support surface is sway-referenced with a gain of 0.25, i.e., it rotates one-fourth as much as the angular changes in orientation of the subject's center of body gravity in relation to the ankles. Changes in the anteroposterior position of center of vertical force (i.e., ankle torque) 32 and the angular displacement of the subject's center of body gravity with respect to the ankles 31 move randomly as the subject stands erect. EMG traces from four ankle and thigh muscles 33 typically show little activity under this quiescent condition. After the subject has stood for a period of time, a brief increase in air pressure 34 is introduced to the normal left ear. Following the pressure stimulus, there is no significant increase in the subject's displacement from equilibrium. The above described procedures are then repeated on the other ear.

In part B of FIG. 3, the rotational position of the support surface is horizontally fixed by setting the sway-reference gain to 0.0. Now, after a period of quiescent standing, the pressure stimulus 34' is introduced to the abnormal right ear. With the surface fixed, however, no postural activity changes correlated with the pressure stimulus are observed in any of the three measurements 31', 32', and 33'.

In part C, the rotational orientation of the support surface is again sway-referenced to the angular orientation of the subject's center of vertical force with a gain of 0.25. Now introduction of the controlled change in external ear canal pressure produces a large postural reaction consisting of rapid and significant changes in the center of vertical force position 31", the angular orientation of the center of body gravity 32", and the leg muscle EMG signals 33".

If a significant postural reaction to pressure stimulation occurs in one or more of the stability measures, then there is a high probability of one or more perilymph fistula and other abnormal coupling between the middle ear and the inner ear in the stimulated ear. The ear is highly unlikely to have a perilymph fistula or other abnormal coupling between the middle ear and the inner ear if there are no significant postural reactions to pressure stimulation under the any of the sway-referenced support surface conditions.

The procedure can also be performed as the subject stands with the rotational axis of the ankles perpendicular to the rotational axes of the support surface. With this standing configuration, the sway-reference conditions are created by rotating the support surface in proportion to the left to right lateral displacements of the subject's center of body gravity in relation to the ankle joints. And, the proceedure can be performed with the subject standing on a support surface with 2 rotational axes, one colinear and one perpendicular to the ankles. With this system, sway-referenced conditions are created by rotating the colinear axis in proportion to the antero-posterior sway rotations of the subject's center of body gravity and the perpendicular axis in proportion to the left to right lateral sway displacements of the subject.

With the support surface held fixed, the three measures of the subject's stability described in FIG. 3 are recorded by the computer for an interval of time sufficient to establish baseline levels of postural activity. After the three activity baselines are established, one or a series of brief pressure change stimuli are introduced to the external canal of one ear, while recording of the three measures of postural activity continues. Then, mean levels of activity in each of the three measures of stability are computed during a fixed time interval following each pressure stimulus.

If a significant reaction to stimulation occurs in one or more of the three measures of stability, then testing of that ear is terminated. If no significant reactions are observed while the subject is standing on the fixed support surface, the above test procedure is repeated with the support surface rotating in proportion to changes in angular orientation of the subject's center of body gravity, i.e., the sway-referenced conditions. First, the support surface is rotated 0.12 times the angular rotation of the subject's center of body gravity, i.e., the 0.12 gain sway-referenced condition, and new baseline levels for the three measures of postural activity are calculated. Then, one or a sequence of brief external canal pressure stimuli are re-introduced to the ear. The methods described above are used again to determine whether or not statistically significant reactions occur in one or all of the measures of postural activity. If reactions are significant, the test is terminated. If no significant reactions occur, the procedure is repeated with the sway-reference gain increased to 0.25, then 0.50, 0.75, and then 1.0.

To perform the perilymph fistula test, the waveform, amplitude, and frequency properties of the pressure stimulus can be varied. The maximum positive and negative pressure amplitudes are limited by patient comfort and safety. The stimulus waveform, however, determines the statistical methods used to identify the presence of postural responses. With discrete pulse stimuli, similar to those shown in FIG. 3, the presence of a postural response can be determined by pulse triggered averaging according to methods well-known in the prior art. With continuously varying pressure stimuli, stimulus-response correlations can be computed also according to means well-known in the prior art.

Figure 6:
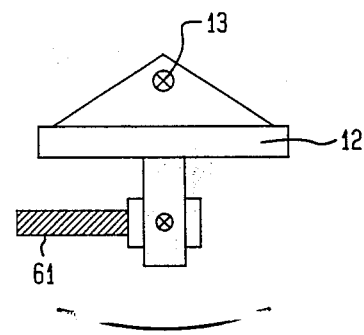
FIG. 6 illustrates a second simpler means for providing a support surface which rotates in functional relation to a quantity related to the subject's displacement from equilibrium.

In the perilymph fistula test, a support surface in which motions are actively controlled by a motor can be replaced with a support surface with viscoelastic compliant properties which moves passively in relation to the displacements of the subject from the maintained equilibrium position. FIG. 6 shows such simpler means for providing a support surface which rotates in functional relation to a quantity related to the subject's displacement from equilibrium. The support surface 12 is made compliant about the axis of rotation 13 by restrasining the rotational motion of the surface with a compliant element 61. The compliant element can have purely elastic properties, such as a linear spring, or it can have a combination of elastic and viscous properties, such as with a spring and fluid damper.

In addition, variables for determining the subject's postural activity other than those described in the preferred embodiments can be used. For example, either one or both of the anteroposterior and side to side lateral changes in orientation of the body can be measured with a potentiometer linked to the body with a belt and flexible coupling. Postural activity can also be determined by measuing the electromyographic activity of one or more muscles providing postural support, using surface electrodes and high gain differential amplification.

What is claimed is:

1. A method for determining whether a subject maintaining an upright standing position in equilibrium while antero-posterior support surface inputs are disrupted has a high probability of perilymph fistula or other abnormal coupling between the middle-ear and the inner-ear, such method comprising:

A. placing the subject in an upright standing position on a support surface which is independently rotatable about an axis co-linear with the ankle joints and having the subject assume a position in equilibrium;

B. measuring changes in the antero-posterior and lateral positions of the center of vertical force and in the angular orientation of the subject's center of body gravity in the antero-posterior plane about an axis defined by the ankle joints (hereinafter termed AP stance orientation angle);

C. causing the support surface to undergo changes in angular orientation so as to be in proportion to the measured change in AP stance orientation angle, thereby reducing or nullifying changes in angle between the AP stance orientation of the subject and the inclination of the support surface;

D. introducing to the external canal of one ear a controlled change in air pressure;

E. determining whether the controlled change in pressure produces a significant change in either one or both of the positions and velocities of the antero-posterior and lateral components of the center of vertical force.

2. A method according to claim 1 for determining whether a subject deprived of all visual orientation inputs and with AP stance orientation inputs disrupted has a high probability of perilymph fistula or other abnormal coupling between the middle-ear and the inner-ear, wherein step A includes the additional step of having the subject close the eyes.

3. A method for determining whether a subject maintaining an upright standing position in equilibrium while lateral support surface inputs are disrupted has a high probability of perilymph fistula, such method comprising:

A. placing the subject in an upright standing position on a support surface which is independently rotatable about an axis perpendicular to the angle joints and having the subject assume a position in equilibrium;

B. measuring changes in the antero-posterior and lateral positions of the center of vertical force and in the lateral plane angular orientation of the subject's center of body gravity about an axis defined by the ankle joints (hereinafter termed the lateral stance orientation angle);

C. causing the support surface to undergo changes in angular orientation so as to be in proportion to the measured change in lateral stance orientation angle, thereby reducing or nullifying changes in angle between the lateral stance orientation of the subject and the inclination of the support surface;

D. introducing to the external canal of one ear a controlled change in air pressure;

E. determining whether the controlled change in pressure produces significant changes in either one or both of the components of vertical force and the lateral stance orientation angle.

4. A method according to claim 3 for determining whether a subject deprived of all visual orientation inputs and with lateral stance orientation inputs disrupted has a high probability of perilymph fistula, wherein step A includes the additional step of having the subject close the eyes.

5. A protocol for determining whether a subject has a high probability of perilymph fistula or other abnormal coupling between the middle ear and the inner ear, the method comprising the following steps:

(A) placing the subject in an upright standing position on a support surface which is independently rotatable about an axis co-linear with the subject's ankle joints;

(B) sway referencing the support surface by:
  (1) measuring changes in the antero-posterior and lateral positions of the center of vertical force and in the angular orientation of the subject's center of body gravity in the antero-posterior plane about and axis defined by the ankle joints (hereinafter termed "AP stance orientation angle"); and
  (2) inducing the support surface to undergo changes in angular orientation so as to be in proportion to the measured change in AP stance orientation angle, thereby reducing or nullifying changes in angle between the AP stance orientation of the subject and the inclination of the support surface (the proportion between the induced changes in angular orientation of the support surface and the measured change in AP stance orientation angle hereinafter termed the "sway-reference gain");

(C) fixing the support surface in a horizontal position by setting the sway-reference gain to 0.0;

(D) having the subject assume a position in equilibrium;

(E) calculating the anteroposterior and lateral positions of the center of vertical force;

(F) calculating the statistical properties of anteroposterior and lateral movements of the center of vertical force;

(G) introducing a series of brief controlled changes in the pressure in the subject's ear canal;

(H) re-calculating the statistical properties of anteroposterior and lateral movements of the center of vertical force;

(I) determining by standard statistical tests whether significant increases have occurred in motions of either one or both of the anteroposterior and lateral center of vertical force positions following imposition of the pressure stimuli, such increases being indicative of a high probability of perilymph fistula;

(J) terminating the protocol if a high probability of perilymph fistula has been indicated;

(K) if a high probability of perilymph fistula has not been indicated, repeating steps (D)–(I) with increasing sway-reference gains until either a high probability of perilymph fistula has been indicated or the sway-reference gain reaches 1.0.

6. A protocol according to claim 5, wherein step (A) includes the additional step of having the subject close the eyes.

* * * * *